United States Patent [19]

Jones et al.

[11] Patent Number: 5,558,840
[45] Date of Patent: Sep. 24, 1996

[54] SPECIMEN CUP HOLDER

[76] Inventors: Timothy B. Jones, 2517 E. Sweetbriar, Edmond, Okla. 73034; Robert D. Jones; Lori D. Jones, both of 2233 Hickory Dr., Ardmore, Okla. 73401

[21] Appl. No.: 499,224

[22] Filed: Jul. 7, 1995

[51] Int. Cl.⁶ .................................................. B01L 9/00
[52] U.S. Cl. ...................... 422/104; 422/99; 422/102; 294/30; 294/31.2; 128/760; 215/395; 215/396; 220/737; 220/738; 220/752; 220/757; 220/758; 220/762; 220/763; 220/764; 220/766
[58] Field of Search ........................ 422/99, 102, 104; 206/217, 438, 569; 215/395, 396, 398; 220/737, 738, 752, 754, 755, 756, 757, 758, 762, 763, 764, 766; 128/760, 761, 767; 294/27.1, 30, 31.2; D24/128, 227, 122

[56] References Cited

U.S. PATENT DOCUMENTS

| | | | |
|---|---|---|---|
| D. 306,648 | 3/1990 | Jones et al. | D24/54 |
| D. 334,804 | 4/1993 | Jones et al. | D24/128 |
| D. 335,178 | 4/1993 | Jones et al. | D24/128 |
| D. 335,179 | 4/1993 | Jones et al. | D24/128 |
| D. 335,180 | 4/1993 | Jones et al. | D24/128 |
| D. 335,346 | 5/1993 | Jones et al. | D24/128 |
| D. 335,708 | 5/1993 | Jones et al. | D24/128 |
| 5,096,669 | 3/1992 | Lauks et al. | 422/61 |
| 5,147,342 | 9/1992 | Kane et al. | 604/356 |
| 5,174,965 | 12/1992 | Jones et al. | 422/102 |
| 5,202,094 | 4/1993 | Jones et al. | 422/102 |
| 5,316,732 | 5/1994 | Golukhov et al. | 422/102 |
| 5,342,330 | 8/1994 | Kane et al. | 604/329 |
| 5,422,076 | 6/1995 | Jones | 422/102 |

*Primary Examiner*—Jill Warden
*Assistant Examiner*—Maureen M. Wallenhorst

[57] ABSTRACT

A device for holding and positioning a specimen cup for collection of a biological specimen with a ring (18) with a handle (14) attached by a hinge (24). The ring (18) receives and securely supports a specimen cup. The hinge (24) allows the handle (14) to assume folded or extended positions relative to the ring (18). The handle (14) extends outward and upward from the ring (18) when in use, thereby, removing one's hand from the specimen cup. One can then more easily hold and position the specimen cup without soiling their hand with the specimen. The hinge (24) also allows the handle (14) to be folded and secured to the ring (18) to facilitate packaging.

5 Claims, 4 Drawing Sheets

SPECIMEN CUP HOLDER

BACKGROUND—CROSS-REFERENCES TO RELATED APPLICATIONS

This invention is related to our design patent application Ser. No. 29/016,716, Filed 1993 Dec. 17 now Des. U.S. Pat. No. 364,458 issued on Nov. 21, 1995.

BACKGROUND—FIELD OF INVENTION

This invention relates to a holding device for specimen cups used in the medical field to collect biological samples from patients.

BACKGROUND—DESCRIPTION OF PRIOR ART

Physician offices, hospitals, and private labs use specimen cups to obtain urine, sputum, and stool samples from patients. Most patients are expected to give biological samples in the privacy of a restroom at the medical facility. Therefore, the patient is expected to hold the specimen cup while the biological sample is obtained. A family member or a medical person often holds the specimen cup for a child or disabled patient. The person holding the specimen cup will often soil their hand when collecting urine or stool specimens. This is particularly a problem for pregnant or obese patients, children, the elderly and many disabled patients. Soiling is also a frequent problem when a patient collects a midstream urine specimen. Midstream samples are often required when a patient's urine is to be cultured for possible infections. Patients are required to begin their urine stream into the toilet or bed pan and then insert the specimen cup into the middle portion of their urine stream so as to obtain an uncontaminated sample.

The problems of hand soiling and of collecting uncontaminated specimens has been addressed by previous specimen cup holding devices. The following patents represent prior attempts to effectively prevent this problem:

Jones et al. Des. U.S. Pat. No. 306,648

Kane et al. U.S. Pat. No. 5,147,342

Jones et al. U.S. Pat. No. 5,174,965

Jones et al. U.S. Pat. No. 5,202,094

Jones et al. Des. U.S. Pat. No. 334,804

Jones et al. Des. U.S. Pat. No. 335,178

Jones et al. Des. U.S. Pat. No. 335,180

Jones et al. Des. U.S. Pat. No. 335,346

Jones et al. Des. U.S. Pat. No. 335,708

However, each of these holding devices have significant disadvantages. The specimen cup holder in our previous U.S. Pat. No. 5,202,094 issued 1993 Apr. 13, requires assembly before it can be used to effectively hold a specimen cup. The specimen cup holder in our previous U.S. Pat. No. 5,174,965 issued 1992 Dec. 29, is difficult and expensive to manufacture. Also, this device cannot be economically packaged with the specimen cup. The systems for collecting urine in U.S. Pat. No. 5,147,342 to Kane et al., 1992 Sep. 15, places the patient's hand horizontal to or below their urine stream thereby increasing the risk of soiling the patient's hand. Also, Kane's device is difficult for most patients to position while seated on a toilet and it cannot be economically packaged with the specimen cup. The specimen cup holder in our previous U.S. Pat. No. Des. 335,346 issued 1993 May 4, attaches to the top of the specimen cup and therefore must be removed after a specimen is collected before a lid can be placed on the specimen cup. The specimen cup holders in our previous Des. U.S. Pat. Nos. 335,178 (1993), 334,804 (1993), 335,179 (1993), elevate the patient's hand above the rim of the specimen cup when used to collect a specimen; however, these devices cannot be economically packaged with the specimen cup. The specimen cup holder in U.S. Pat. No. Des. 306,648 to Jones et al., 1990 Mar. 13, places the patient's hand horizontal to or below their urine stream and it cannot be economically packaged with the specimen cup. The specimen cup holders in our design U.S. Pat. Nos. 335,708 (1993) and 335,180 (1993) do elevate the patient's hand above the specimen cup and they both can be economically packaged with the specimen cup by being in a folded position. However, these specimen cup holders do not have a means to secure them in a folded position.

OBJECTS AND ADVANTAGES

Accordingly, several objects and advantages of our specimen cup holder are:

(a) to provide a specimen cup holder which will elevate one's hand above the rim of the specimen cup while collecting a specimen;

(b) to provide a specimen cup holder which will elevate one's hand above their urine stream;

(c) to provide a specimen cup holder which will allow one to easily and securely position a specimen cup to receive a urine sample while seated on a toilet;

(d) to provide a specimen cup holder which will allow a one seated on a toilet to keep their hand above the toilet seat while collecting a urine sample;

(e) to provide a specimen cup holder which is economical to manufacture;

(f) to provide a specimen cup holder which has a hinge that allows its handle to fold;

(g) to provide a specimen cup holder whose handle can be secured in a folded position;

(h) to provide a specimen cup holder which can be economically packaged with individually wrapped specimen cups.

Further objects and advantages of our specimen cup holder will become apparent from a consideration of the drawings and ensuing description.

DESCRIPTION OF THE DRAWINGS

In the drawings, closely related figures have the same number but different alphabetic suffixes.

FIG. 5G is a perspective view of securing grooves near the end of a specimen cup holder handle.

LIST OF REFERENCE NUMERALS

8 Specimen Cup Holder
10 Traction Means
11 Securing Portion
12 Gripping Portion
13 Gripping Portion End
14 Handle
15 Handle Sidewall
15A Handle Sidewall
16 Extending Portion
17 Handle Face
21 Ring Thickness
22 Proximal Portion
23 Inside Diameter
24 Hinge Means
25 Handle Hinge Stop
26 Outside Surface
27 Ring Hinge Stop
Interface
Securing Half-Cylinder
Securing Mound
18 Ring
9 Inside Surface
20 Distal Portion
32 Securing Ridge
33 Securing Groove
33A Securing Groove

DESCRIPTION—FIGS. 1 TO 5

Figure 1:
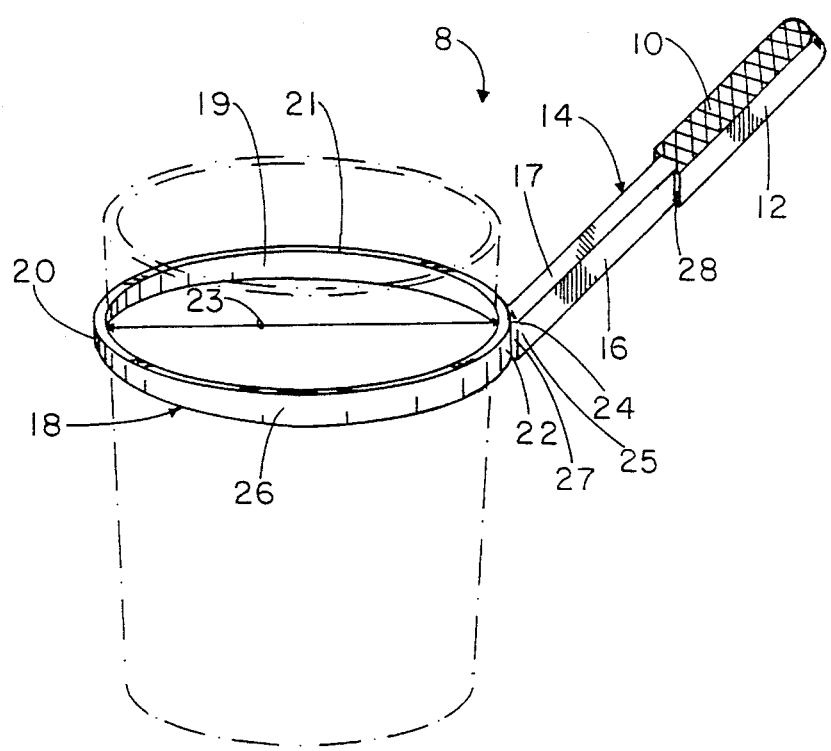
FIG. 1 is a perspective view of a specimen cup holder with the handle in a fully extended position.

FIG. 1 shows a perspective view of a specimen cup holder 8. Specimen cup holder 8 is comprised of a handle 14 connected to a ring 18 by a hinge means 24. Handle 14 has a gripping portion 12 and an extending portion 16 separated by an interface 28. Handle 14 also has a traction means 10 on a handle face 17 of gripping portion 12. In the preferred embodiment illustrated in FIG. 1., traction means 10 consists of a crosshatch of parallel raised lines. Handle face 17 also comprises part of extending portion 16. A handle hinge stop 25 is the proximal end of extending portion 16. Hinge means 24 connects handle hinge stop 25 to a ring hinge stop 27. Ring hinge stop 27 is connected to a proximal portion 22 of ring 18. Proximal portion 22 is opposite a distal portion 20 of ring 18. Ring 18 is also comprised of an outside surface 26 and an inside surface 19. Ring 18 has a ring thickness 21 and an inside diameter 23. Inside diameter 23 is of predetermined size so that inside surface 19 securely holds a specimen container inserted into ring 18.

Figure 2:
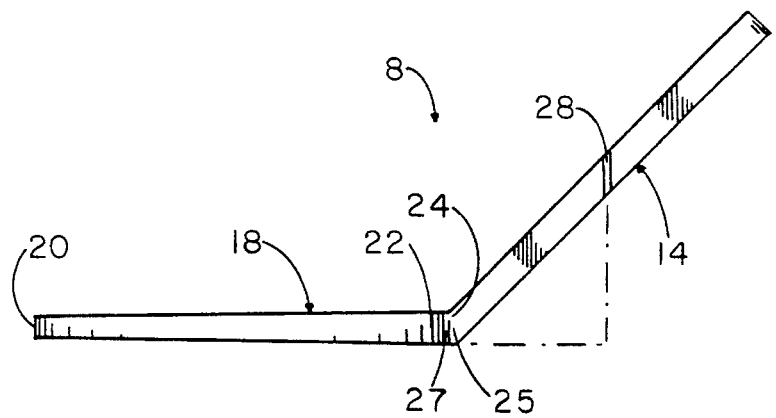
FIG. 2 is a side view of a specimen cup holder with the handle in a fully extended position.

FIG. 2 shows a side view of specimen cup holder 8. Handle hinge stop 25 and ring hinge stop 27 are engaged when handle 14 is in a fully extended position as illustrated. Interface 28 is substantially perpendicular to the long axis of ring 18 when handle 14 is in a fully extended position. Distal portion 20 is shorter than proximal portion 22 with the height of ring 18 uniformly tapered between proximal portion 22 and distal portion 20.

Figure 3:
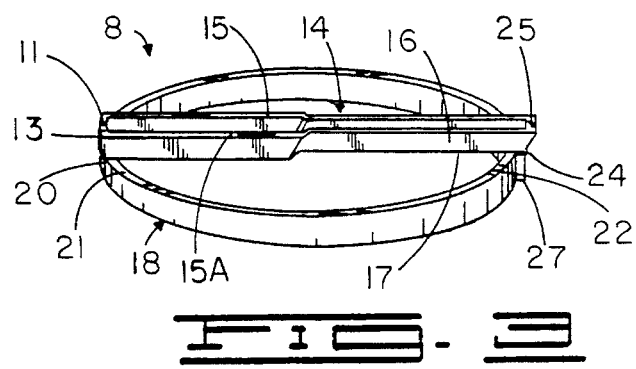
FIG. 3 is a perspective view of a specimen cup holder with the handle in a folded position.

FIG. 3 shows a perspective view of specimen cup holder 8 with handle 14 in a folded position. Specimen cup holder 8 can be constructed of any material that can be bent without fracturing, such as polypropylene, polyethylene, polystyrene or various plasticized materials. Hinge means 24 allows handle 14 to assume folded and extended positions relative to ring 18. Gripping portion end 13 rests on distal portion 20 in a folded position illustrated in FIG. 3. Handle hinge stop 25 forms an obtuse angle with handle face 17. Handle hinge stop 25 and ring hinge stop 27 are separated when handle 14 is in a folded position. Handle 14 is comprised of a handle sidewall 15 and a handle sidewall 15A connected by handle face 17, gripping portion end 13, and handle hinge stop 25. Sidewalls 15 and 15A, end 13, hinge stop 25, and ring thickness 21 are of similar thickness. A securing portion 11 is the underneath surface of gripping portion end 13.

Figure 4:
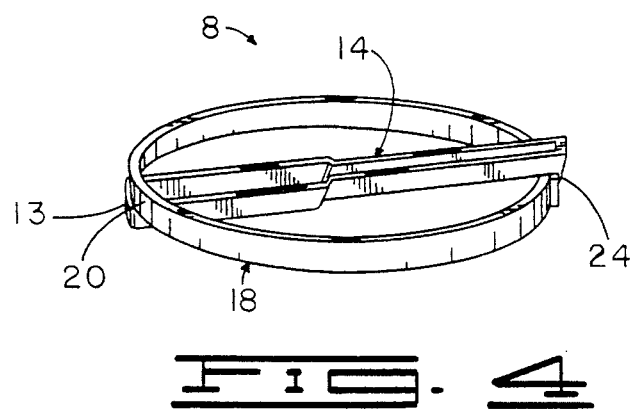
FIG. 4 is a perspective view of a specimen cup holder with the handle in a secured position.

FIG. 4 shows a perspective view of specimen cup holder 8 with handle 14 in a secured position. Since specimen cup holder 8 is constructed of flexible material, gripping portion end 13 can assume a position below distal portion 20.

Figures 5A, 5B:
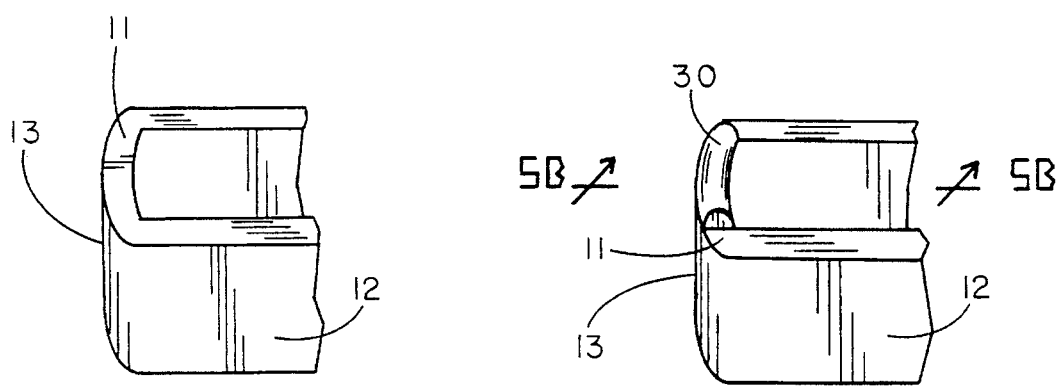
FIG. 5A is a perspective view of the end of a specimen cup holder handle.
FIG. 5B to 5F show various embodiments of raised securing means on the end of a specimen cup holder handle.

FIG. 5A shows a perspective view of the end of gripping portion 12. Securing portion 11 is shown without a securing means present.

Figure 5C:
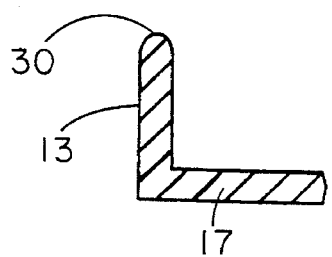
Figure 5D:
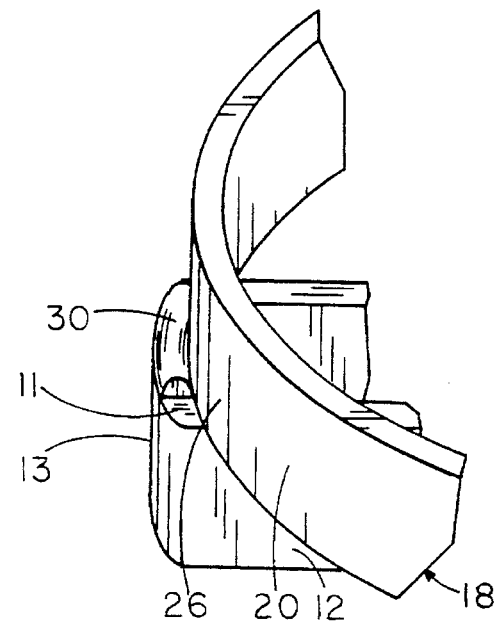
Figure 5E:
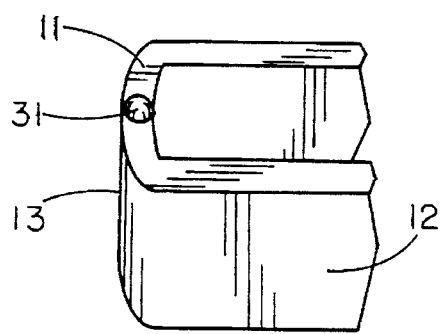
Figure 5F:
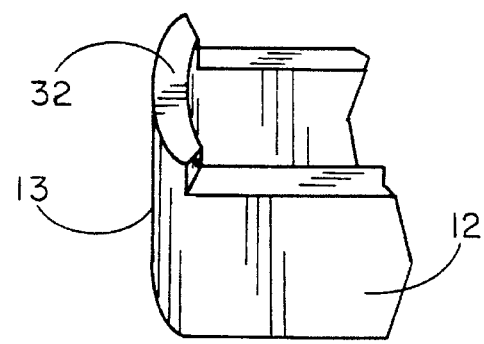
Figure 56:
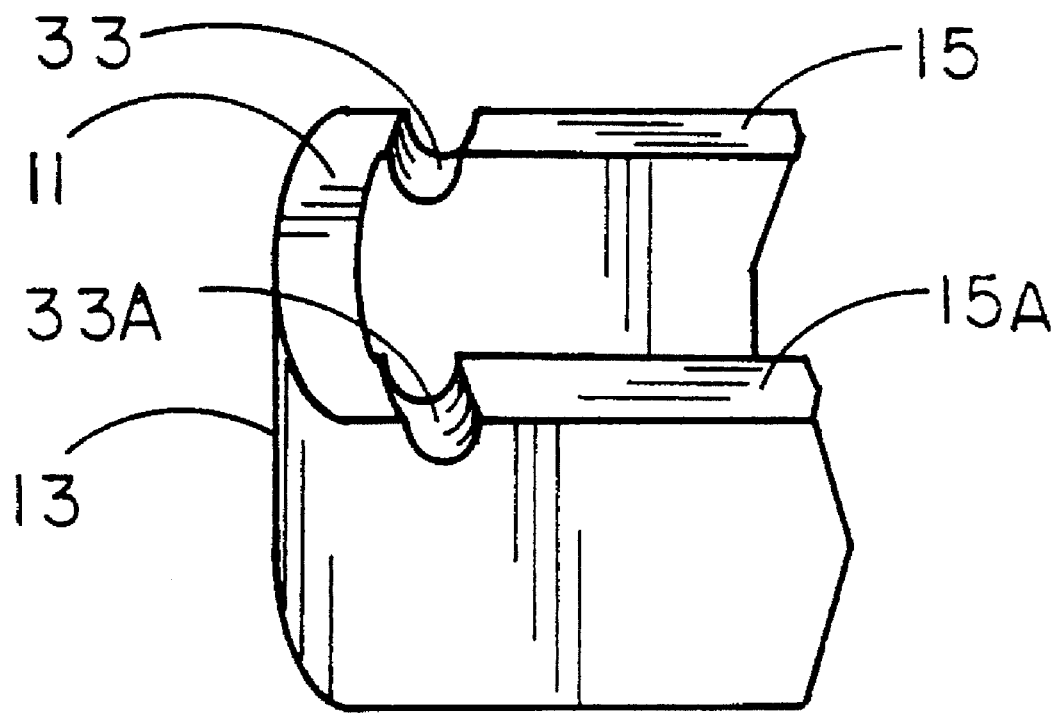

FIG. 5B through FIG. 5F illustrate various possible securing means on securing portion 11. FIG. 5B shows a perspective view of a securing half-cylinder 30. FIG. 5C shows a side sectional view of securing half-cylinder 30 taken generally along line 5B—5B in FIG. 5B. Handle face 17 and gripping portion end 13 are of similar thickness. FIG. 5D shows a perspective view of securing half-cylinder 30 with a cut away of ring 18 in a secured position. Outside surface 26 presses against half-cylinder 30 and distal portion 20 presses against gripping portion 12. FIG. 5E shows a perspective view of a securing mound 31. FIG. 5F shows a perspective view of a securing ridge 32. FIG. 5G shows a perspective view of a securing groove 33 in handle sidewall 15 and a securing groove 33A in handle sidewall 15A.

From the description above, a number of advantages of our specimen cup holder become evident:

(a) The specimen cup holder allows one's hand to be elevated above and away from a specimen cup.

(b) The specimen cup holder's gripping portion 12 and traction means 10 allow one to securely hold and position a specimen cup.

(c) The specimen cup holder allows one to sit on a toilet seat and obtain a urine specimen without placing one's hand below the toilet seat.

(d) The specimen cup holder can be economically manufactured. A simple two part injection mold can produce the specimen cup holder with handle 14 in an extended position because of the angle between interface 28 and ring 18. The similar thickness of sidewalls 15 and 15A, gripping end 13, handle face 17, handle hinge stop 25, and ring 18 allows efficient injection molding. The tapered height of ring 18 from proximal portion 22 to distal portion 20 decreases the amount of material required to manufacture the specimen cup holder.

(e) The specimen cup holder can be folded and secured in a folded position to allow economical packaging as well as packaging with individually wrapped specimen cups.

OPERATION—FIGS. 1, 3, 4, 5

Handle 14 is extended outward away from ring 8 by hinge means 24 to a fully extended position as illustrated in FIG. 1. A fully extended position is achieved when handle hinge stop 25 and ring hinge stop 27 are engaged. The obtuse angle formed by handle hinge stop 25 and handle face 17 assures that handle 14 projects outward and upward from ring 18. A specimen container is placed into inside diameter 23 and inside surface 19 engages and holds the specimen container. One grasps distal portion 12 to support and position specimen cup holder 8 and an engaged specimen cup to collect a specimen. Hinge means 24 is of sufficient thickness and strength to support ring 18, a specimen cup, and a specimen without tearing apart. Traction means 10 provides increased traction for the one's fingers to grasp distal portion 12.

As shown in FIG. 3, hinge means 24 allows handle 14 to assume a folded position when handle 14 is flexed toward ring 18. A folded position allows for economical packaging.

Handle 14 can also assume a secured position as shown in FIG. 4. A secured position is achieved by flexing handle 14 until gripping portion end 13 rests on distal portion 20. The flexible material of specimen cup holder 8 allows one to distort ring 18 in an elongated fashion parallel to the long axis of handle 14. One can then further flex handle 14 until gripping portion end 13 is below the long axis of ring 18. Ring 18 is then allowed to reassume a non-distorted circular shape, thereby positioning distal portion 20 above gripping portion end 13. The elastic quality of hinge means 24 presses distal portion 20 against gripping portion end 13.

FIGS. 5B–5F show various raised securing means present on securing portion 11. In the preferred embodiment, securing half-cylinder 30 is the securing means. To secure handle 14 to ring 18, one positions gripping portion end 13 below distal portion 20 as described previously. One then distorts ring 18 in an elongated fashion perpendicular to the long axis of handle 14 until outside surface 26 opposes securing means 30. Ring 18 is then released and the elastic quality of ring 18 presses outside surface 26 against securing means 30 as illustrated in FIG. 5D. Simultaneously, the elastic quality of hinge means 24 presses gripping portion 12 against distal portion 20, thus holding handle 14 and ring 18 in a secured position. Securing mound 31 and securing ridge 32 operate in a similar manner by opposing surface 26 when handle 14 and ring 18 are in a secured position.

Instead of a raised securing means, grooves or other recessed securing means present on gripping portion 12 can be used to hold handle 14 and ring 18 in a secured position. FIG. 5G illustrates grooves 33 and 33A in sidewalls 15 and 15A of distal portion 12. Distal portion 20 fits into grooves 33 and 33A to hold handle 14 and ring 18 in a secured position.

CONCLUSION, RAMIFICATIONS, AND SCOPE OF INVENTION

Accordingly, the reader will see that the specimen cup holder of this invention allows one to securely hold and position a specimen container while collecting a specimen without soiling one's hand with the specimen. The relatively uniform sidewall thickness of the specimen cup holder, the tapering design of the height of the ring, and the relationship of the handle interface with the ring all contribute to economical and efficient manufacturing. In addition, the hinge allows the handle to be folded and the securing means holds the handle in a folded position to facilitate packaging.

Although the description above contains many specificities, these should not be construed as limiting the scope of the invention but as merely providing illustrations of some of the presently preferred embodiments of this invention. For example, the traction means could have other patterns, ornamental designs, lettering, or any raised projections to provide traction for a user's fingers. Furthermore, the traction means could consist of a pattern of recesses in the handle face of the gripping portion. The gripping portion of the handle could be circular, oval, square, or triangular. Also, the securing means could be any type of elevation, hook, knob, or ridge on the handle or any type of groove or notch in the handle that would contact and oppose the distal portion of the ring. Further, the handle could be substantially longer that that shown in the illustrations but still be capable of securing with the ring because of the flexible properties of the ring.

Thus the scope of the invention should be determined by the appended claims and their legal equivalents, rather than by the examples given.

We claim:

1. A device for holding a specimen container comprising:
   (a) a ring of predetermined size sufficient to supportingly engage a specimen container,
   (b) a handle,
   (c) a hinge means for joining said ring and said handle whereby said ring and said handle can assume different relative positions to one another,
   (d) a securing means for holding the handle and the ring in an opposingly engaged, folded position opposite the side of the ring from the hinge means, said securing means located on a lower surface near an end of the handle distal to the hinge means, the length of the handle being substantially the same as an outer diameter of the ring such that the end of the handle aligns with the ring opposite the hinge means when the handle is folded parallel to the ring, the hinge means and the ring being made of a flexible material such that the ring may be elongated parallel to the long axis of the handle allowing the end of the handle to be positioned below the plain of the lower surface of the ring opposite the hinge means, the ring being allowed to resume a substantially circular configuration, the securing means and the ring being brought into contact with one another by the elastic quality of the hinge means and the ring to produce an opposingly engaged, folded position between the handle and the ring.

2. The device of claim 1 wherein said securing means is a raised projection on the end of said handle, and wherein the securing means presses against the outer and lower surface of the ring which is without any complementary recess or projection.

3. The device of claim 1 wherein said securing means is a plurality of raised projections on the end of said handle, and wherein the securing means presses against the outer and lower surface of the ring which is without any complementary recesses or projections.

4. The device of claim 1 wherein said securing means is a recess on the end of said handle, and wherein the securing means presses against the outer and lower surface of the ring which is without any complementary recess or projection.

5. The device of claim 1 wherein said securing means is a plurality of recesses on the end of said handle, and wherein the securing means presses against the outer and lower surface of the ring which is without any complementary recesses or projections.

* * * * *